(12) United States Patent
Lockridge

(10) Patent No.: US 9,339,482 B2
(45) Date of Patent: May 17, 2016

(54) METHODS TO TREAT DYSREGULATED BLOOD GLUCOSE DISORDERS

(71) Applicant: REGENTS OF THE UNIVERSITY OF MINNESOTA, Minneapolis, MN (US)

(72) Inventor: Amber Dianne Lockridge, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/550,824

(22) Filed: Nov. 21, 2014

(65) Prior Publication Data

US 2015/0150836 A1   Jun. 4, 2015

Related U.S. Application Data

(60) Provisional application No. 61/907,935, filed on Nov. 22, 2013.

(51) Int. Cl.
| | | |
|---|---|---|
| *A61K 31/198* | (2006.01) | |
| *A61K 38/28* | (2006.01) | |
| *A61K 45/06* | (2006.01) | |
| *A61K 31/42* | (2006.01) | |
| *A61K 9/00* | (2006.01) | |
| *A61K 9/20* | (2006.01) | |
| *A61K 9/48* | (2006.01) | |

(52) U.S. Cl.
CPC ............. *A61K 31/198* (2013.01); *A61K 9/0019* (2013.01); *A61K 9/2018* (2013.01); *A61K 9/2054* (2013.01); *A61K 9/4858* (2013.01); *A61K 31/42* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | |
|---|---|---|
| 4,559,157 A | 12/1985 | Smith |
| 4,608,392 A | 8/1986 | Jacquet |
| 4,820,508 A | 4/1989 | Wortzman |
| 4,938,949 A | 7/1990 | Borch |
| 4,992,478 A | 2/1991 | Geria |
| 7,211,557 B2 | 5/2007 | DiMarchi et al. |
| 2011/0275683 A1 | 11/2011 | Graul |

FOREIGN PATENT DOCUMENTS

| | | |
|---|---|---|
| CN | 102834108 A | 12/2012 |
| EP | 2085120 A1 | 5/2009 |
| WO | 2005066135 A2 | 7/2005 |
| WO | 2008087035 A2 | 7/2008 |
| WO | 2012104852 A1 | 8/2012 |
| WO | 2013029762 A1 | 3/2013 |

OTHER PUBLICATIONS

Balamurugan et al., "Islet Isolation from Pancreatitis Pancreas for Islet Autotransplantation", The Islets of Langerhans, 2nd Edition 42, 1-25 (2014).
Bank, "Rapid assessment of islet viability with acridine orange and propidium iodide", In Vitro Cell Dev Biol 24, 266-273 (1988).
Cryer et al., "Hypoglycemia in diabetes", Diabetes Care 26 (6), 1902-1912 (2003).
Doyle et al., "Pharmacological agents that directly modulate insulin secretion", Pharmacological Reviews 55 (1), 105-131 (2003).
Duplantier et al., "Discovery, SAR, and pharmacokinetics of a novel 3-hydroxyquinolin-2(1H)-one series of potent D-amino acid oxidase (DAAO) inhibitors", J Med Chem 52 (11), 3576-3585 (2009).
Emilov et al., "A pilot double-blind comparison of d-serine and high-dose olanzapine in treatment-resistant patients with schizophrenia", Schizophr Res 150, 604-605 (2013).
Ferraris et al., "Synthesis and biological evaluation of D-amino acid oxidase inhibitors", J. Med. Chem. 51 (12), 3357-3359 (2008).
Fukasawa et al., "Identification and characterization of a Na(+)-independent neutral amino acid transporter that associates with the 4F2 heavy chain and exhibits substrate selectivity for small neutral D- and L-amino acids", J Biol Chem 275, 9690-9698 (2000).
Fukushima et al., "Glutamate exocrine dynamics augmented by plasma glutamine and the distribution of amino acid transporters of the rat pancreas", J Physiol Pharmacol 61, 265-271 (2010).
Gonoi et al., "Functional neuronal ionotropic glutamate receptors are expressed in the non-neuronal cell line MIN6", J Biol Chem 269, 16989-16992 (1994).
Groop, "Pathogenesis of type 2 diabetes: the relative contribution of insulin resistance and impaired insulin secretion", Int J Clin Pract Suppl 113, 3-13 (2000).
Gustafson et al., "Retinal NMDA receptor function and expression are altered in a mouse lacking D-amino acid oxidase", J Neurophysiol 110, 2718-2726 (2013).
Hashimoto, "Free D-serine, D-aspartate and D-alanine in central nervous system and serum in mutant mice lacking D-amino acid oxidase", Neurosci Letters 152, 33-36 (1993).
Horio et al., "Levels of D-serine in the brain and peripheral organs of serine racemase (Srr) knock-out mice", Neurochem Int 59, 853-859 (2011).
Imai et al., "Whole body autoradiographic study on the distribution of 14C-D-serine administered intravenously to rats", Amino Acids 15, 351-361 (1998).
Jursky et al., "Developmental expression of the glycine transporters GLYT1 and GLYT2 in mouse brain", J Neurochem 67, 336-346 (1996).

(Continued)

*Primary Examiner* — Amber D Steele
*Assistant Examiner* — Schuyler Milton
(74) *Attorney, Agent, or Firm* — Viksnins Harris & Padys PLLP

(57) ABSTRACT

The invention provides methods and compositions for treating dysregulated blood glucose disorders.

17 Claims, 14 Drawing Sheets

(56) References Cited

OTHER PUBLICATIONS

Kanahara et al., "Glycine and D: -serine, but not D: -cycloserine, attenuate prepulse inhibition deficits induced by NMDA receptor antagonist MK-801", Psychopharmacology 198, 363-374 (2008).
Katane et al., "Identification of novel D-amino acid oxidase inhibitors by in silico screening and their functional characterization in vitro", J Med Chem 56, 1894-1907 (2013).
Konno et al., "Mutant mice and rats lacking D-amino acid oxidase", Chem Biodivers 7, 1450-1458 (2010).
Lin et al., "Cloning of the cDNA for the human NMDA receptor NR2C subunit and its expression in the central nervous system and periphery", Mol Brain Res 43, 57-64 (1996).
Lockridge et al., "Timing-dependent reduction in ethanol sedation and drinking preference by NMDA receptor co-agonist d-serine", Alcohol 46, 389-400 (2012).
Miyoshi et al., "Simultaneous two-dimensional HPLC determination of free D-serine and D-alanine in the brain and periphery of mutant rats lacking D-amino-acid oxidase", J. Chromatography B 879, 3184-3189 (2011).
Molnar et al., "Identification of functional ionotropic glutamate receptor proteins in pancreatic beta-cells and in islets of Langerhans", FEBS Lett 371, 253-257 (1995).
Mothet et al., "D-serine is an endogenous ligand for the glycine site of the N-methyl-D-aspartate receptor", PNAS 97, 4926-4931 (2000).
Nakauchi et al., "Cloning and characterization of a human brain Na(+)-independent transporter for small neutral amino acids that transports D-serine with high affinity", Neurosci Lett 287, 231-235 (2000).
Papas et al., "Human islet oxygen consumption rate and DNA measurements predict diabetes reversal in nude mice", Am J Transplant 7, 707-713 (2007).
Rustenbeck, "Desensitization of insulin secretion", Biochem Pharma 63, 1921-1935 (2002).
Sacchi et al., "D-amino acid oxidase inhibitors as a novel class of drugs for schizophrenia therapy", Curr Pharm Des. 19 (14), 2499-2511 (2013).
Shao et al., "Functional and immunocytochemical characterization of D-serine transporters in cortical neuron and astrocyte cultures", J Neurosci Res 87, 2520-2530 (2009).
Sparey et al., "The discovery of fused pyrrole carboxylic acids as novel, potent D-amino acid oxidase (DAO) inhibitors", Biorg Med Chem Lett 18, 3386-3391 (2008).
Tornovsky-Babeay et al., "Type 2 diabetes and congenital hyperinsulinism cause DNA double-strand breaks and p53 activity in β cells", Cell Metab 19, 109-121 (2014).
Triplett et al., "Examining the mechanisms of glucose regulation", Am J Manag Care 18, S4-S10 (2012.).
Wake et al., "Exaggerated responses to chronic nociceptive stimuli and enhancement of N-methyl-D-aspartate receptor-mediated synaptic transmission in mutant mice lacking D-amino-acid oxidase", Neurosci Letters 297, 25-28 (2005).
Nolosker et al., "Purification of serine racemase: biosynthesis of the neuromodulator D-serine", Proc Natl Acad Sci 96, 721-725 (1999).
Marquard et al., "Characterization of pancreatic NMDA receptors as possible drug targets for diabetes treatment", Nature Medicine vol. 21 (4), 363-372 with 4 Supplemental pages (2015).
Durrant et al., "D-Serine in Neuropsychiatric Disorders: New Advances", Advances in Psychiatry, Article ID 359735, 16 pages (2014).
Inagaki et al., "Expression and role of ionotropic glutamate receptors in pancreatic islet cells", FASEB J. 9, 686-691 (1995).
Krentz et al., "Octreotide: A Long-Acting Inhibitor of Endogenous Hormone Secretion for Human Metabolic Investigations", Metabolism vol. 43 (1), 24-31 (1994).
Nong et al., "Glycine binding primes NMDA receptor internalization", Nature vol. 422, 302-307 (2003).
Almond et al., "Behavioral and biochemical characterization of a mutant mouse strain lacking D-amino acid oxidase activity and its implications for schizophrenia", Mol. Cell Neurosci. 32, 324-334 (2006).
Tsai et al., "A genome-wide association study identifies susceptibility variants for type 2 diabetes in Han Chinese", PLoS Genet 6 (2), e1000847, 9 pages (2010).
Okamoto et al., "Endogenous hydrogen sulfide protects pancreatic beta-cells from a high-fat diet-induced glucotoxicity and prevents the development of type 2 diabetes", Biochemical and Biophysical Research communications, vol. 44v2, 227-233 (2013).
Krug et al., "Why is d-serine nephrotoxic and α-aminoisobutyric acid protective?" American Journal of Physiology-Renal Physiology 293. 1, F382-F390 (2007).
Williams et al., "Sodium benzoate attenuates d-serine induced nephrotoxicity in the rat", Toxicology, vol. 207, 35-48 (2005).

METHODS TO TREAT DYSREGULATED BLOOD GLUCOSE DISORDERS

CROSS-REFERENCE TO RELATED APPLICATIONS

This patent application claims the benefit of priority of U.S. application Ser. No. 61/907,935, filed Nov. 22, 2013, which application is herein incorporated by reference.

GOVERNMENT FUNDING

This invention was made with government support under contract number 08656017 awarded by the National Institutes of Health. The government has certain rights in the invention.

BACKGROUND OF THE INVENTION

Glucose is the primary energy source used by mammalian cells to sustain themselves and to accomplish their basic functions. Glucose can be introduced into the blood stream from dietary absorption, the breakdown of the glycogen (a glucose storage molecule) or the endogenous production of glucose from other raw materials (gluconeogenesis). The uptake of glucose into and out of the blood, through which it can be circulated throughout the body, is a critical homeostatic system, regulated by a diverse range of metabolic pathways. Healthy adult blood glucose typically ranges between 70-99 mg/dL, with the potential to spike as high as 140 mg/dL following a meal (Triplett, C. L. et al. (2012), Am J Manag Care 18, S4-S10). Blood sugar levels that fall above (hyperglycemia) or below (hypoglycemia) the typical ranges can lead to a variety of debilitating acute or chronic symptoms including but not limited to loss-of-consciousness, impaired vision, weight gain/loss, changes in consumptive behavior (hunger and thirst), neuropathy, cardiovascular dysfunction and even death. There are a number of diseases, pathological conditions and medications that can result in transient or persistent blood sugar dysregulation (Triplett, 2012). The blood glucose dysregulation disorder, diabetes melitus, is actually a cluster of metabolic diseases (including type I, type II, gestational diabetes and prediabetes) characterized by hyperglycemia. On the other hand, the primary treatment for diabetic hyperglycemia, insulin administration, can trigger an overreaction leading to potentially severe and life-threatening hypoglycemia, limiting the treatment options for some people (Cryer et al., (2003), Diabetes Care 26(6), 1902-1912). Thus there is a need for improved methods and agents to treat dysregulated blood glucose disorders such as hyperglycemia, hypoglycemia and diabetes.

The most critical and well-studied factor for regulating blood glucose (i.e., blood sugar) is the hormone insulin. Insulin reduces blood sugar by facilitating glucose transport into target cells, encouraging its conversion into glycogen and lipid storage, and by indirectly inhibiting gluconeogenesis in the liver (Triplett, 2012). Insulin is secreted by β-cells, which are a component of the pancreatic mini-organs, the islets of Langerhans (i.e. islets). A fundamental contributing cause of diabetes is diminished insulin secretion caused by a progressive loss of β-cell function and mass (Groop L., (2000). Int J Clin Pract Suppl 113, 3-13). β-cells are activated by a cascade of reactions, starting with the passage of glucose molecules through a transporter into the cell where its subsequent metabolism leads to a depolarization of the cell (i.e., an increase in positively charged ions). This depolarization activates voltage-dependent calcium (Ca+) channels that open to let in a flood of Ca+. The incoming Ca+ wave triggers exocytosis of the insulin-containing secretory vesicles out into the extracellular space. When blood glucose rises, more β-cell metabolites are produced, which then exaggerate the depolarization/Ca+ influx and increase the total insulin secretion back into the blood stream (Doyle, M. E. et al., (2003). Pharmacological Reviews 55(1), 105-131).

D-serine is an endogenous amino acid, derived from dietary consumption and from the racemization of L-serine through the enzyme serine racemase (Konno, R., et al., (2010), Chem Biodivers 7, 1450-1458; Miyoshi, Y., et al., (2011), J Chromatogr B Analyt Technol Biomed Life Sci 879, 3184-3189; Wolosker, H., et al., (1999), Proc Natl Acad Sci USA 96, 721-725). Although traditionally studied as a central nervous system (CNS) neurotransmitter, D-serine has been localized to the pancreas in both mice (~11 pmol/mg tissue; Horio, M., et al., (2011), Neurochem Int 59, 853-859) and rats (~15 nmol/g tissue; Imai, K., et al., (1998), Amino Acids 15, 351-361; Miyoshi, 2011). Intravenous injection of $C^{14}$-labelled D-serine predominantly concentrated in the pancreas after 30 minutes, compared to the other peripheral organs examined in the rat (Imai et al., 1998). In the brain, extracellular D-serine uptake is primarily mediated by two transporter proteins (Shao, Z., et al., (2009), J Neurosci Res 87, 2520-2530) asc-1, which has also been observed in mouse (Fukasawa, Y., et al., (2000), J Biol Chem 275, 9690-9698) and human (Nakauchi, J., et al., (2000), Neurosci Lett 287, 231-235) pancreas and ASCT2, which is expressed in rat islets (Fukushima, D., et al., (2010), J Physiol Pharmacol 61, 265-271). The glycine transporter, GlyT1, which is critical for the maintenance of D-serine regulated synapses in the CNS, has also been found in the embryonic mouse pancreas (Jursky, F., and Nelson, N., (1996), J of Neurochem 67, 446-44). Furthermore, D-amino acid oxidase (DAO), D-serine's primary catabolic enzyme, appears to be active in the pancreas such that the DAO mutant rat demonstrates a 10-fold increase in pancreatic D-serine (Miyoshi, 2011). Despite these findings, the functional role of D-serine in the pancreas has not been examined.

D-serine's dominant function in the CNS is as a co-agonist of the N-methyl-D-aspartate (NMDA) receptor (NMDAR) (Mothet, J-P., et al., (2000), PNAS 97, 4926-4931). These ionotropic glutamate receptors are activated by a convergence of coincident events including local depolarization, binding of the primary glutamate ligand, and requisite binding of a co-agonist typically resulting in a large depolarization of the post-synaptic cell through an influx of Na+ and Ca+ ions. The NMDAR is a heterotetrameric structure with two prerequisite GLUN1 co-agonist binding subunits and, most commonly, two glutamate-binding GLUN2 subunits, types A-D. While predominantly distributed in the CNS, functional NMDARs have also been located in peripheral organs, including the pancreas. GLUN2C cDNA was detected in human pancreatic tissue (Lin, Y. J., et al., (1996), Mol Brain Res 43, 57-64) and several subunit proteins (GLUN1, GLUN2C and GLUN2D) have been observed in multispecies β-cell lines (Gonoi, T., et al., (1994), J Biol Chem 269, 16989-16992; Molnar, E., et al., (1995), FEBS Lett 371, 253-257) and isolated rat islets (Molnar, 1995).

Currently there is a need for agents and/or methods that are useful for treating dysregulated blood glucose disorders. There is also a need for agents and/or methods that are useful for modulating blood glucose levels.

SUMMARY OF THE INVENTION

D-Serine has been found to modulate glucose levels in the blood when dosed in a mammal. Accordingly, D-serine may be useful for treating dysregulated blood glucose disorders (e.g., hyperglycemia and diabetes).

One embodiment provides a method for treating a dysregulated blood glucose disorder (e.g., hyperglycemia and diabetes) in a mammal (e.g., a human) in need thereof comprising administering an effective amount an N-methyl-D-aspartate receptor activator (e.g., D-serine, D-cycloserine or glycine) or a pharmaceutically acceptable salt thereof to the mammal.

One embodiment provides a method for treating a dysregulated blood glucose disorder (e.g., hyperglycemia and diabetes) in a mammal (e.g., a human) in need thereof comprising administering an effective amount an N-methyl-D-aspartate receptor activator (e.g., D-serine, D-cycloserine or glycine) or a pharmaceutically acceptable salt thereof to the mammal, wherein the N-methyl-D-aspartate receptor activator is an agonist at the glycine binding site.

One embodiment provides a method for treating a dysregulated blood glucose disorder (e.g., hyperglycemia and diabetes) in a mammal (e.g., a human) in need thereof comprising administering an effective amount of an N-methyl-D-aspartate receptor activator or a pharmaceutically acceptable salt thereof to the mammal, wherein the N-methyl-D-aspartate receptor activator binds to the glycine binding site.

One embodiment provides a method for treating a dysregulated blood glucose disorder (e.g., hyperglycemia and diabetes) in a mammal (e.g., a human) in need thereof comprising administering an effective amount of D-serine, or a pharmaceutically acceptable salt thereof to the mammal.

One embodiment provides a pharmaceutical composition comprising D-serine or a pharmaceutically acceptable salt thereof, insulin and a pharmaceutically acceptable carrier.

One embodiment provides a pharmaceutical composition comprising D-serine or a pharmaceutically acceptable salt thereof, one or more D-amino acid oxidase inhibitors or pharmaceutically acceptable salts thereof and a pharmaceutically acceptable carrier.

One embodiment provides a pharmaceutical composition comprising D-serine or a pharmaceutically acceptable salt thereof, one or more antidiabetic agents or pharmaceutically acceptable salts thereof and a pharmaceutically acceptable carrier.

One embodiment provides D-serine or a pharmaceutically acceptable salt thereof for use in the therapeutic or prophylactic treatment of a dysregulated blood glucose disorder (e.g., hyperglycemia, hypoglycemia and diabetes)

One embodiment provides the use of D-serine or a pharmaceutically acceptable salt thereof for the manufacture of a medicament for the treatment of a dysregulated blood glucose disorder (e.g., hyperglycemia, hypoglycemia and diabetes) in a mammal (e.g., a mammal).

One embodiment provides a method for treating a dysregulated blood glucose disorder (e.g., hyperglycemia, and diabetes) in mammal (e.g., a human) in need thereof comprising administering an effective amount of an agent that alters endogenous D-serine levels (e.g., a DAO inhibitor that raises D-serine levels), or a pharmaceutically acceptable salt thereof to the mammal.

One embodiment provides a pharmaceutical composition comprising a DAO inhibitor or a pharmaceutically acceptable salt thereof, insulin and a pharmaceutically acceptable carrier.

One embodiment provides an effective amount of an agent that alters endogenous D-serine levels (e.g., a DAO inhibitor that raises D-serine levels) or a pharmaceutically acceptable salt thereof for use in the therapeutic or prophylactic treatment of a dysregulated blood glucose disorder (e.g., hyperglycemia, hypoglycemia and diabetes)

One embodiment provides the use of an effective amount of an agent that alters endogenous D-serine levels (e.g., a DAO inhibitor that raises D-serine levels) or a pharmaceutically acceptable salt thereof for the manufacture of a medicament for the treatment of a dysregulated blood glucose disorder (e.g., hyperglycemia, hypoglycemia and diabetes) in a mammal (e.g., a mammal).

DETAILED DESCRIPTION

Figure 1:
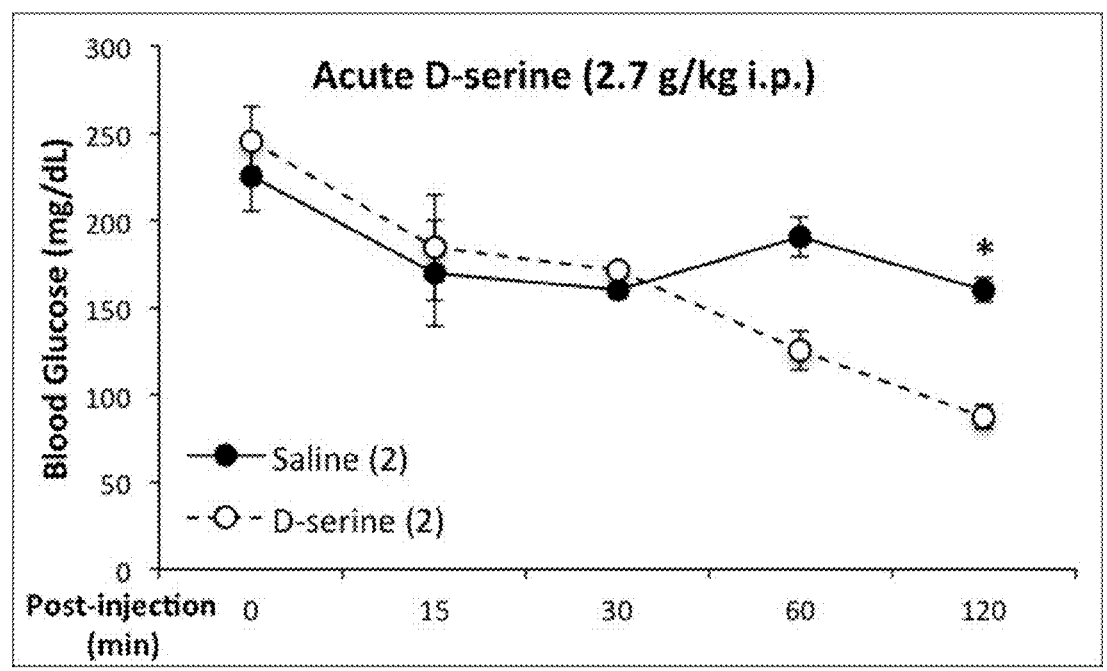
FIG. 1 illustrates the effect of D-serine on blood glucose in wildtype mice after acute administration.

It has been found that administration of D-serine can modulate levels of blood glucose. It has been demonstrated that D-serine can lower blood glucose levels and increase islet insulin secretion. Therefore, it may be possible to treat dysregulated blood glucose disorders in which blood glucose levels are above or below normal (or acceptable) values or ranges and/or insulin secretion is insufficient or impaired and/or glucose sensitivity is diminished by administering D-serine or an agent that modulates endogenous levels of D-serine. D-Serine or an agent that modulates endogenous levels of D-serine may also be useful for treating other diseases, conditions or symptoms that are linked to or caused or exacerbated by a dysregulated blood glucose disorder including but not limited to weight control.

In one embodiment the dysregulated blood glucose disorder is hyperglycemia. In one embodiment the dysregulated blood glucose disorder is diabetes. In one embodiment the N-methyl-D-aspartate receptor activator (e.g., D-serine) or the pharmaceutically acceptable salt thereof is administered prior to eating.

It may be beneficial to administer an N-methyl-D-aspartate receptor activator (e.g., D-serine) with insulin. Insulin is used to treat certain dysregulated blood glucose disorders. Administration of insulin with an N-methyl-D-aspartate receptor activator (e.g., D-serine) may allow for the insulin to be administered at a lower dose (e.g., lower amount) than when insulin is administered in the absence of the N-methyl-D-aspartate receptor activator (e.g., D-serine). Administration of an N-methyl-D-aspartate receptor activator (e.g., D-serine) with insulin may also be beneficial in patients with insulin resistance. Accordingly, one embodiment provides a method for treating a dysregulated blood glucose disorder comprising the administration (e.g., co-administration) of an N-methyl-D-aspartate receptor activator (e.g., D-serine) or a pharmaceutically acceptable salt thereof and insulin to a mammal (e.g., a human) in need thereof. Another embodiment provides a composition comprising an N-methyl-D-aspartate receptor activator (e.g., D-serine) or a pharmaceutically acceptable salt thereof, insulin and a pharmaceutically acceptable carrier. Another embodiment provides a kit comprising an N-methyl-D-aspartate receptor activator (e.g., D-serine) or a pharmaceutically acceptable salt thereof, insulin, packaging material, and instructions for administering the D-serine with the insulin.

It may also be beneficial to administer an N-methyl-D-aspartate receptor activator (e.g., D-serine) with one or more D-amino acid oxidase inhibitors. Accordingly, one embodiment provides a method for treating a dysregulated blood glucose disorder comprising the administration (e.g., co-administration) of an N-methyl-D-aspartate receptor activator (e.g., D-serine) or a pharmaceutically acceptable salt thereof and one or more D-amino acid oxidase inhibitors or pharmaceutically acceptable salts thereof to a mammal (e.g., a human) in need thereof. Another embodiment provides a composition comprising an N-methyl-D-aspartate receptor activator (e.g., D-serine) or a pharmaceutically acceptable salt thereof, one or more D-amino acid oxidase inhibitors or pharmaceutically acceptable salts thereof and a pharmaceutically acceptable carrier. The invention also provides a kit comprising an N-methyl-D-aspartate receptor activator (e.g., D-serine) or a pharmaceutically acceptable salt thereof, one or more D-amino acid oxidase inhibitors or pharmaceutically acceptable salts thereof, packaging material, and instructions for administering the N-methyl-D-aspartate receptor activator (e.g., D-serine) with the D-amino acid oxidase inhibitor(s).

Another embodiment provides a method for treating a dysregulated blood glucose disorder comprising the administration (e.g., co-administration) of an N-methyl-D-aspartate receptor activator (e.g., D-serine) or a pharmaceutically acceptable salt thereof, one or more D-amino acid oxidase inhibitors or pharmaceutically acceptable salts thereof and insulin to a mammal (e.g., a human) in need thereof. Another embodiment provides a composition comprising an N-methyl-D-aspartate receptor activator (e.g., D-serine) or a pharmaceutically acceptable salt thereof, one or more D-amino acid oxidase inhibitors or pharmaceutically acceptable salts thereof, insulin and a pharmaceutically acceptable carrier. The invention also provides a kit comprising an N-methyl-D-aspartate receptor activator (e.g., D-serine) or a pharmaceutically acceptable salt thereof, one or more D-amino acid oxidase inhibitors or pharmaceutically acceptable salts thereof, insulin, packaging material, and instructions for administering the N-methyl-D-aspartate receptor activator (e.g., D-serine) with the D-amino acid oxidase inhibitor(s) and the insulin.

N-Methyl-D-Aspartate (NMDA) Receptor Activators.

D-Serine is a co-agonist of the N-methyl-D-aspartate (NMDA) receptor (NMDAR) and binds to the glycine site of the NMDA receptor. Accordingly, other agents that activate the NMDA receptor, including other agents that do so by acting as agonists at the glycine site of the NMDA receptor, may be useful for the treatment of dysregulated blood glucose disorders. Thus, the term NMDA receptor activator includes any agent (e.g., any molecular entity) that activates the NMDA receptor irregardless of the mechanism by which it activates the receptor. Such N-methyl-D-aspartate (NMDA) receptor activators include but are not limited to D-serine, glycine and D-cycloserine (PCT/IL2012/050034 which document is hereby incorporated by reference in its entirety) including pharmaceutically acceptable salts thereof. In one embodiment the NMDA receptor activator is an agent that is a co-agonist of the receptor. In one embodiment the NMDA receptor activator is an agent that binds to the glycine binding site of the NMDA receptor. In one embodiment the NMDA receptor activator is an agent that binds to the glycine binding site of the NMDA receptor and functions as an agonist of the NMDA receptor. In one embodiment the NMDA receptor is expressed in the pancreas. As used herein the term "binds" means that the agent interacts (e.g., has affinity) for the receptor. In one embodiment the $IC_{50}$ (or Ki) of the agent for the receptor (e.g., the glycine binding site of the NMDA receptor) is less than or about equal to 10 mM; in one embodiment the $IC_{50}$ (or Ki) is less than or about equal to 1 mM; in one embodiment the $IC_{50}$ (or Ki) is less than or about equal to 100 µM; in one embodiment the $IC_{50}$ (or Ki) is less than or about equal to 10 µM; in one embodiment the $IC_{50}$ (or Ki) is less than or about equal to 1 µM; in one embodiment the $IC_{50}$ (or Ki) is less than or about equal to 100 nM; in one embodiment the $IC_{50}$ (or Ki) is less than or about equal to 10 nM in one embodiment the $IC_{50}$ (or Ki) is less than or about equal to 1 nM.

One embodiment provides a method for treating a dysregulated blood glucose disorder (e.g., hyperglycemia, and diabetes) in a mammal (e.g., a human) in need thereof comprising administering an effective amount of an N-methyl-D-aspartate (NMDA) receptor activator (e.g., a co-agonist of the NMDA receptor such as a co-agonist of the glycine binding site), or a pharmaceutically acceptable salt thereof to the mammal. One embodiment provides a method for treating a dysregulated blood glucose disorder (e.g., hyperglycemia, and diabetes) in a mammal (e.g., a human) in need thereof comprising administering an effective amount of an agent or a pharmaceutically acceptable salt thereof where the agent binds to the glycine binding site of the N-methyl-D-aspartate (NMDA) receptor, or a pharmaceutically acceptable salt thereof to the mammal. One embodiment provides a method for treating a dysregulated blood glucose disorder (e.g., hyperglycemia, and diabetes) in a mammal (e.g., a human) in need thereof comprising administering an effective amount of an agent that is a co-agonist of the glycine binding site of the NMDA receptor, or a pharmaceutically acceptable salt thereof to the mammal.

Dysregulated Blood Glucose Disorder.

As used herein the term dysregulated blood glucose disorder refers to a disease, condition symptom or side-effect (e.g., medication) wherein blood glucose levels are above or below the normal levels or above or below normal level ranges. In one embodiment the dysregulated blood glucose disorder refers to a disease, condition symptom or side-effect (e.g., medication) wherein blood glucose levels are above normal levels or above normal level ranges. Therefore, the treatments described herein include treating a disease or disorder that directly or indirectly causes the dysregulation of blood glucose (e.g., high or low blood glucose) as well as treating the condition dysregulation of blood glucose (e.g., high or low blood glucose) wherein the condition is a symptom or side-effect of a disease or disorder or wherein the condition is a side-effect of medication.

In one embodiment the dysregulated blood glucose disorder is hyperglycemia. The treatments described herein include the treatment of hyperglycemia, (including chronic or transient hyperglycemia) that is caused by pancreatitis, pancreatic cancer, hyperthyroidism, Cushing's syndrome, tumors related to hormone secretion (e.g. glucagonoma, pheochromocytoma), severe stress episodes (e.g., heart attack, stroke, trauma, severe illness), certain medications including prednisone, estrogens, beta-blockers, glucagon, oral contraceptives, phenothiazines, pregnancy and diabetes including insulin deficiency and resistance to insulin.

In one embodiment the dysregulated blood glucose disorder is diabetes (type I diabetes, type II diabetes, gestational diabetes, pre-diabetes condition in which dysregulated blood glucose is a symptom).

The methods described herein can be useful for treating or preventing dysregulated blood glucose disorders. The term "treatment" or "treating," to the extent it relates to a disorder, disease, condition, symptom or side-effect includes inhibiting the disorder, disease, condition, symptom or side-effect, and/or eliminating the disorder, disease, condition, symptom or side-effect, and/or relieving one or more symptoms of the disorder, disease or condition or side effect. The term "preventing" or 'prevention" includes preventing the disorder, disease, condition, symptom or side-effect from occurring.

D-Amino Acid Oxidase Inhibitors.

D-Amino acid oxidase (DAO or DAAO) inhibitors are compounds that inhibit the action D-amino acid oxidase. DAO inhibitors raise the level of D-serine by blocking the metabolism of D-serine by inhibiting D-amino acid oxidase. Thus, it may be beneficial to administer an NMDA receptor activator (e.g., D-serine) as described herein with one or more DAO inhibitors. Accordingly one embodiment provides a method to treat a dysregulated blood glucose disorder in a mammal (e.g., a human) in need thereof comprising administration of an NMDA receptor activator (e.g., D-serine) or a pharmaceutically acceptable salt thereof to the mammal with one or more DAO inhibitors or a pharmaceutically acceptable salt thereof as described herein below. One embodiment provides a method to treat a dysregulated blood glucose disorder in a mammal (e.g., a human) in need thereof comprising administration of a DAO inhibitor or a pharmaceutically acceptable salt thereof as described herein below to the mammal.

One embodiment provides DAO inhibitors disclosed in J. Med. Chem. 2013, 56, 1894 which document is hereby incorporated by reference in its entirety. One embodiment provides a DAO inhibitor selected from (E)-3-(3-hydroxyphenyl) acrylic acid, thiophene-2-carboxylic acid, 3-hydroxy-2H-chromen-2-one, 5,6-dihydro-4H-cyclopenta[b]thiophene-2-carboxylic acid, 5-(o-tolyl)-1,3,4-oxadiazol-2-ol, 4-ethyl-5-propylthiophene-2-carboxylic acid, 5-methyl-4-propylthiophene-2-carboxylic acid, 4-ethyl-5-methylthiophene-2-carboxylic acid, 4,5,6,7-tetrahydrobenzo[b]thiophene-2-carboxylic acid and 5-phenyl-1,3,4-oxadiazol-2-ol and pharmaceutically acceptable salts thereof.

One embodiment provides DAO inhibitors disclosed in Current Pharmaceutical Design, 2013, 19, 2499-2511, which document is hereby incorporated by reference in its entirety. One embodiment provides a DAO inhibitor selected from 5-methylpyrazole-3-carboxyxlic acid, 6-chloro benzo[d] isooxazol-3-ol, 4H-furo[3,2-b]pyrrole-5-carboxyxlic acid, 4H-thieno[3,2-b]pyrrole-5-carboxylic acid, 3-hyroxyquinolin-2(1H)-one, 5-chloro-3-hydoxy-4a,5-dihydro-1,8-naphthyridin-2(1H)-one and 5-chloro-3-hydoxy-4a,5-dihydro-1,8-naphthyridin-2(1H)-one and pharmaceutically acceptable salts thereof.

One embodiment provides DAO inhibitors disclosed in J. Med. Chem. 2009, 52, 3576-3585, which document is hereby incorporated by reference in its entirety. One embodiment provides a DAO inhibitor selected from:

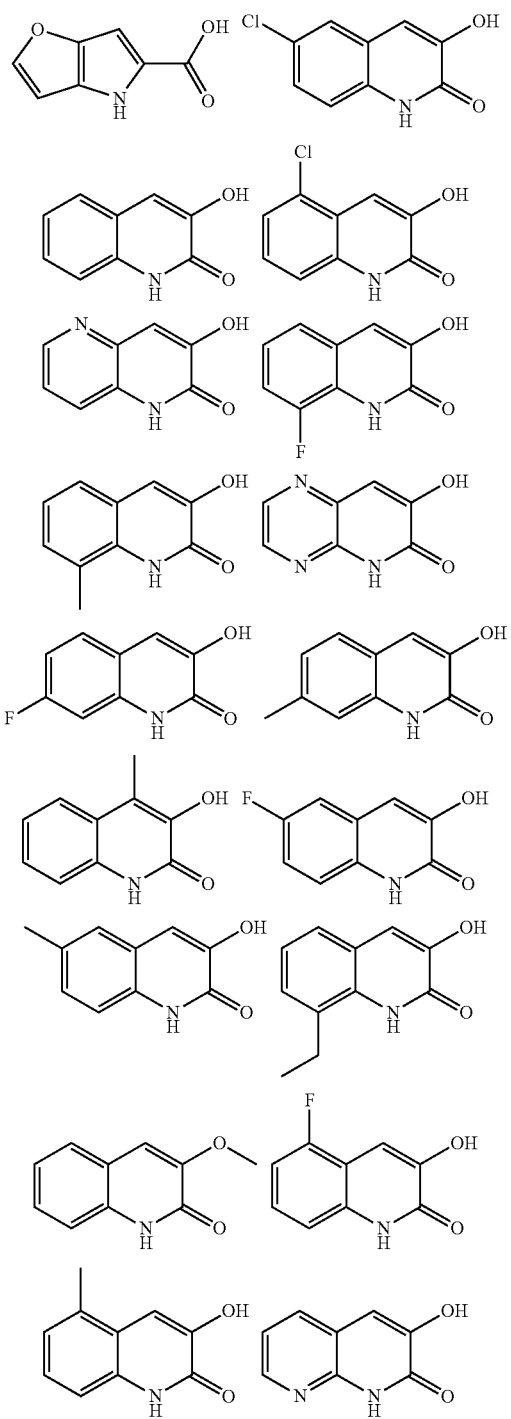

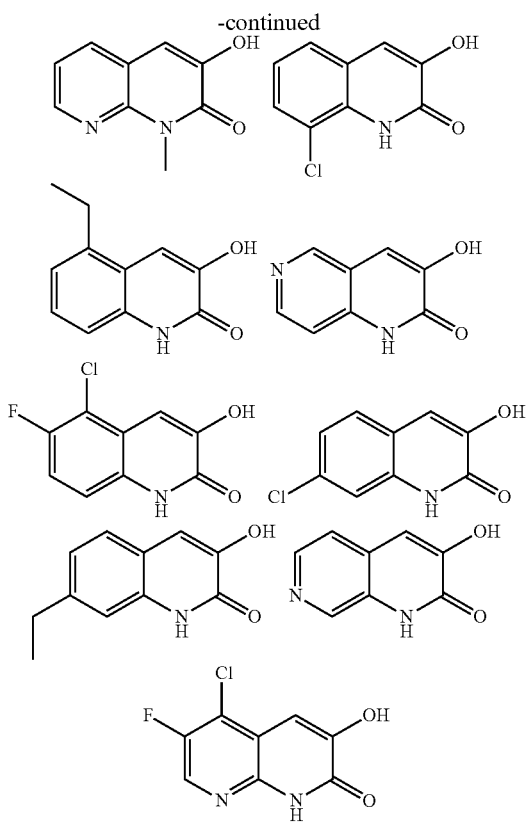

and pharmaceutically acceptable salts thereof

One embodiment provides DAO inhibitors disclosed in J. Med. Chem. 2008, 51, 3357-3359 which document is hereby incorporated by reference in its entirety. One embodiment provides a DAO inhibitor selected from a compound described in the table below wherein $R^4$, $R^5$, $R^6$ and $R^7$ have the specified values:

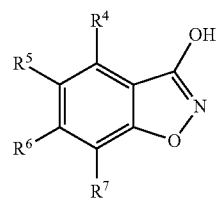

| $R^4$ | $R^5$ | $R^6$ | $R^7$ |
|---|---|---|---|
| H | H | H | H |
| $CF_3$ | H | H | H |
| F | H | H | H |
| H | Br | H | H |
| H | I | H | H |
| H | $NO_2$ | H | H |
| H | H | F | H |
| H | H | Cl | H |
| H | H | $CH_3$ | H |
| H | H | OMe | H |
| H | H | OEt | H |
| H | H | $NO_2$ | H |
| H | H | $CF_3$ | H |
| H | H | $CF_3$ | F |
| H | H | H | F |
| H | H | H | $CH_3$ | and pharmaceutically acceptable salts thereof.

One embodiment provides DAO inhibitors disclosed in Biorg. Med. Chem. Lett. 2008, 18, 3386-3391 which document is hereby incorporated by reference in its entirety. One embodiment provides a DAO inhibitor selected from:

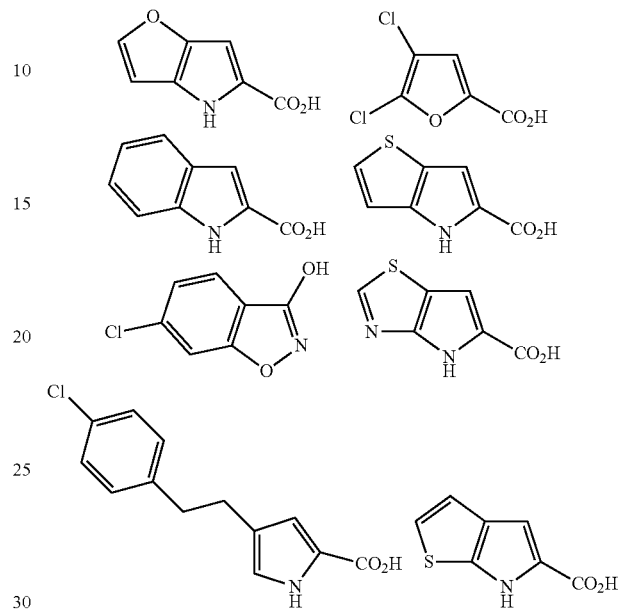

and pharmaceutically acceptable salts thereof.

One embodiment provides DAO inhibitors selected from sodium benzoate and acyclovir and pharmaceutically acceptable salts thereof.

Antidiabetic Agents.

The methods described herein can also include the optional administration of one or more antidiabetic agents with an NMDA receptor activator (e.g., D-serine). Thus, it may be beneficial to administer D-serine (as described herein) with one or more antidiabetic agents. Accordingly one embodiment provides a method for treating a dysregulated blood glucose disorder in a mammal (e.g., a human) in need thereof comprising administering an effective amount of an NMDA receptor activator (e.g., D-serine) or a salt thereof and an antidiabetic agent to the mammal. Another embodiment provides a method for treating a dysregulated blood glucose disorder in a mammal (e.g., a human) in need thereof comprising administering an effective amount of an NMDA receptor activator (e.g., D-serine) or a salt thereof and an antidiabetic agent and optionally insulin and/or a DAO inhibitor to the mammal. Antidiabetic agents include insulin sensitizers and agents the boost insulin secretion such as but not limited to biguanidines (e.g., metformin), meglitinides, sulfonylureas, thizolidinediones, alpha-glucosidase inhibitors, incretins. In one embodiment the antidiabetic agent is an orally administered antidiabetic agent.

Salts.

Administration of an NMDA receptor activator (e.g., D-serine) or a DAO inhibitor or an antidiabetic agent as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutical Compositions and Administration.

An NMDA receptor activator (e.g., D-serine) or the combinations described herein (e.g., an NMDA receptor activator such as D-serine in a combination with a DAO inhibitor and/or insulin and/or an antidiabetic agent) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, an NMDA receptor activator (e.g., D-serine) or the combinations described herein, when suitable, may be systemically administered, e.g., orally, in combination with a pharmaceutically acceptable vehicle or carrier such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

An NMDA receptor activator (e.g., D-serine) or the combinations described herein may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, an NMDA receptor activator (e.g., D-serine) or the combinations described herein may be administered to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of an NMDA receptor activator (e.g., D-serine) or the combinations described herein can be determined by comparing their in vitro activity, and in vivo activity in animal models. Methods for the extrapolation of effective dosages in mice, and other animals, to humans are known to the art; for example, see U.S. Pat. No. 4,938,949.

The amount of an NMDA receptor activator (e.g., D-serine) or a salt (e.g., pharmaceutically acceptable salt) or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 75 mg/kg, or about 3 to about 50 mg/kg, or about 6 to about 90 mg/kg, or about 30 to about 60 mg/kg/day.

An NMDA receptor activator (e.g., D-serine) either alone or as part of a combination as described herein can be conveniently formulated in unit dosage form; for example, containing 5 to 1000 mg, or 10 to 750 mg, or, 50 to 500 mg of D-serine per unit dosage form. In one embodiment, a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As used herein, the term "co-administer" or "co-administration" refers to administration of two or more agents within a 24 hour period of each other, by the same or different routes, for example, as part of a clinical treatment regimen. In one embodiment, "co-administer" refers to administration within 8 hours of each other. In one embodiment, "co-administer" refers to administration within 4 hours of each other. In one embodiment, "co-administer" refers to administration within 2 hours of each other. In one embodiment "co-administer" refers to administration within 30 minutes of each other. In one embodiment, "co-administer" refers to administration within 15 minutes of each other. In one embodiment, "co-administer" refers to administration at the same time, either as part of a single formulation or as multiple formulations that are administered by the same or different routes.

Combination Therapy.

As discussed herein an NMDA receptor activator (e.g., D-serine) can optionally be administered (e.g., co-administer (ed) or co-administration) in combination with other therapeutic agents such DAO inhibitors and/or insulin and/or antidiabetic agents or pharmaceutically acceptable salts thereof. An NMDA receptor activator (e.g., D-serine) can also be optionally be administered in combination with other therapeutic agents such DAO inhibitors and/or insulin and/or diabetic agents such as insulin sensitizers and agents the boost insulin secretion such as but not limited to biguanidines (e.g., metformin), meglitinides, sulfonylureas, thizolidinediones, alpha-glucosidase inhibitors, incretins.

Accordingly, in one embodiment the invention also provides a composition comprising an NMDA receptor activator (e.g., D-serine) or a pharmaceutically acceptable salt thereof, at least one other agent (e.g., a DAO inhibitors and/or insulin and/or another therapeutic agent), and a pharmaceutically acceptable carrier. Another embodiment the invention provides a composition comprising an NMDA receptor activator (e.g., D-serine) or a pharmaceutically acceptable salt thereof, at least one other agent (e.g., a DAO inhibitors and/or insulin and/or diabetic agents such as insulin sensitizers and agents the boost insulin secretion such as but not limited to biguanidines (e.g., metformin), meglitinides, sulfonylureas, thizolidinediones, alpha-glucosidase inhibitors, incretins, and a pharmaceutically acceptable carrier. The invention also provides a kit comprising D-serine, or a pharmaceutically acceptable salt thereof, at least one other agent, packaging material, and instructions for administering D-serine or the pharmaceutically acceptable salt thereof and the other agent or agents to mammal (e.g., a human) to treat hyperglycemia.

Diagnostics.

One embodiment provides for monitoring levels of D-serine (e.g., blood levels and/or plasma levels) in a mammal (e.g., a human) to indicate dysregulated blood glucose disorders such as hyperglycemia, hypoglycemia or diabetes or to indicate the pre-disposition or pre-conditions to such disorders including pre-diabetic conditions. Genotypic variations in genes encoding products pertaining to the synthesis, catabolism, trafficking or other regulation of the levels and activity of D-serine, including but not limited to serine racemase and/or D-amino acid oxidase, may also be evaluated which may indicate a predisposition to a dysregulated blood-glucose disorder such as diabetes including subtypes of diabetes or phenotypic variations such as obese or lean diabetes.

The invention will now be illustrated by the following non-limiting Examples.

Example 1

A. General Procedure for Blood Glucose Testing

Mice were fasted for 4-6 hours. The tails were wiped with ethanol and allowed to dry. For a first time test, the tip of the tail was removed with a scissors. For subsequent tests, a needle was used to puncture the tail vein. The first drop of blood was wiped away and then the second drop was placed on a glucometer test strip. A second test was administered immediately and most scores were an average of the two readings. If there was more than a 100 unit discrepancy between the two readings, a third reading was taken and the reported value was an average of the three.

B. Study of the Effects of D-Serine in Wildtype Mice

Acute Exposed Hypoglycemia.

Four adult male mice of the ddY strain were fasted for 6 hours before testing. A blood glucose reading from each mouse was determined at the start (time 0). The mice were weighed and the average weight was used with an injection volume of 0.3 mL to calculate the concentration of D-serine to dissolve into saline. The dose, 2.7 g/kg, was picked based on previously published behavior studies in which the intraperitoneal dose was the most reliable in inducing a mouse behavior response during pre-pulse startle inhibition (Kanahara, N., et al., (2008), Psychopharmacology, 198, 363-374) and acute ethanol sedation (Lockridge, A., et al., (2012), Alcohol, 46:389-400). After time 0 testing, each mouse received either D-serine or saline (alternating by cage) at 5 minute intervals. Blood glucose readings were taken at 15, 30, 60 and 120 minutes after each mouse's initial injection. The data presented is the average blood glucose (mg/dL), determined by glucometer as previously described (FIG. 1). Each data point is the average of the two mice with the same treatment condition, while the standard error bars indicate the degree of individual variability between subjects. The saline injected control mice (black) maintained a steady glucose level (70-80% of baseline) throughout the testing period. The D-serine injected mice maintained a stable blood sugar at 15 and 30 minutes but demonstrated acute hypoglycemia with a reduction in blood sugar to 52 and 36% of baseline at 60 and 120 minutes, respectively. This data is consistent with the hypothesis that acute administration of D-serine suppresses blood sugar.

Chronic Exposed Hyperglycemia.

Figure 2:
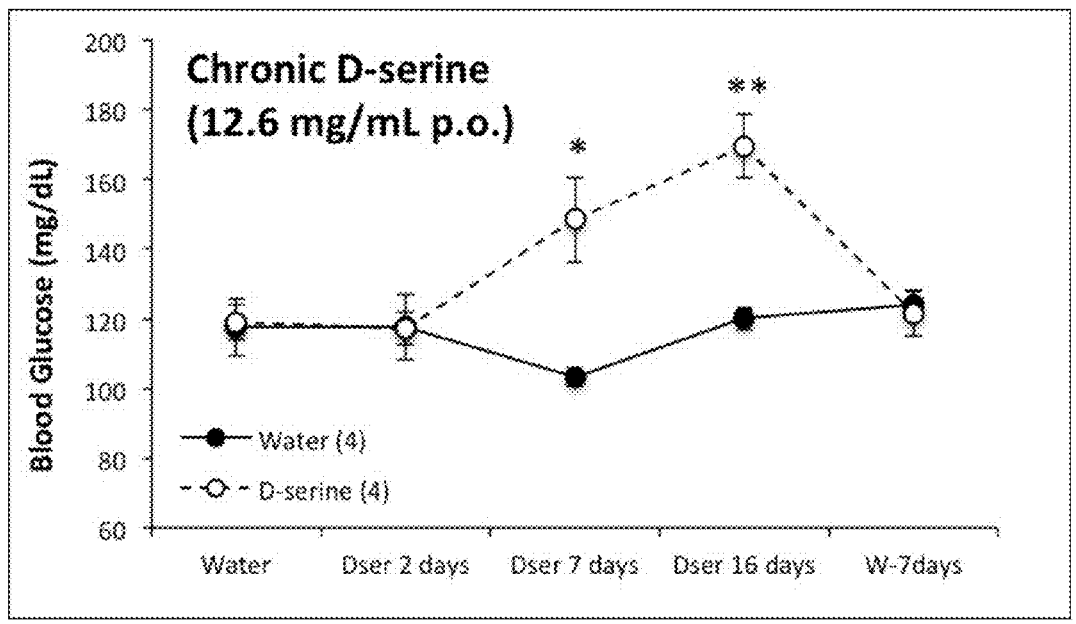
FIG. 2 illustrates the effect of D-serine on blood glucose in wildtype mice after chronic, sustained, administration.

Eight adult male mice of the C57 strain were tested in a chronic administration model. Mice were housed 2 per cage, with each cage outfitted with 2 special drinking tubes (50 mL conical+stopper with sipper tube) to minimize the impact of any problems with a single tube. Two cages of mice drank tap water and two cages of mice drank a D-serine solution (12.6 mg/ml in tap water), with solutions replaced every other day. Every other day, the food and drinking bottles were weighed to determine cage-wide consumptive behaviors and the mice were individually weighed. At specified intervals, mice were also tested for core body temperature by rectal probe and for 4-hours fasted blood glucose. All mice started with a week of water drinking. The first x-axis category shows baseline blood glucose on the day 1 of water drinking (values given as absolute measures, mg glucose/dl of blood) (FIG. 2). After one week, two cages (4 mice) were switched to D-serine solution. Testing two days after the switch showed that blood glucose was still at baseline levels, indicating that 48 hours of D-serine ingestion at this concentration was not sufficient to alter unstimulated, basal blood glucose. After 7 days of D-serine drinking, the treated mice showed elevated blood sugar (103±3 mg/dl water vs. 149±12 mg/dl D-serine), which persisted at 16 days of drinking (120±3 water vs 170±9 D-serine). After this measure, all mice were again switched back to water. After a week of water drinking, the treated mice had recovered back to baseline glucose levels. The water-only control mice did not show significant changes in average blood sugar at any time point. Data also indicate that D-serine drinking mice also demonstrate weight loss during the first week of treatment, possibly influenced by reduced eating (hypophagia) over that time period. Solution drinking was also increased for treated mice (polydipsia). Both acute weight loss and increased drinking are prominent symptoms of the onset of diabetes.

C. Study of Systemic D-Serine Availability in Ethanol Treated Mice

Acute Administration.

Figure 3:
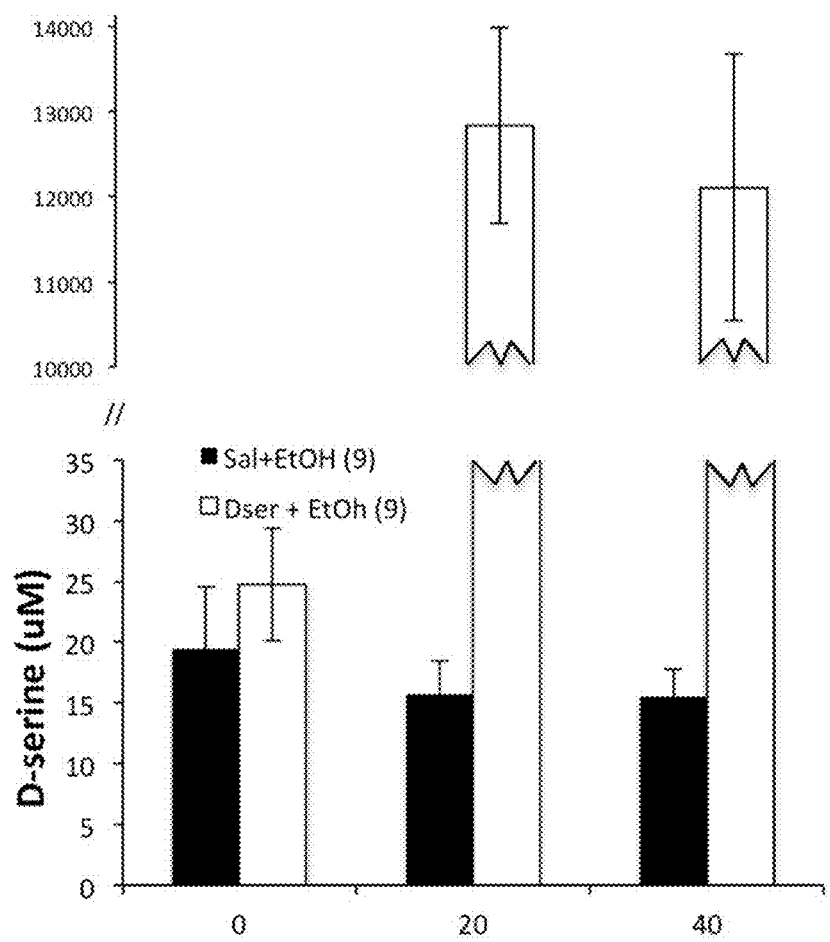
FIG. 3 demonstrates the blood plasma level of D-serine following acute administration.

The data from FIG. 3 serves as an example of a concentration reference value subject to the time frame and administration technique of the acute hypoglycemia experiments described in FIG. 1. A 20 uL blood sample was collected from the facial vein of mice prior to any treatment (time 0) and 20 and 40 minute intervals after an i.p. injection of ethanol (3 g/kg). A pre-treatment injection of saline (n=9) or D-serine (2.7 g/kg, i.p., n=9) was administered 15 minutes before ethanol such that the reported values also correspond to time 35 and 55 minutes after the pre-injection. These blood samples were assayed for D-serine using capillary electrophoresis, as described in the publication (Lockridge, 2012). Basal levels of plasma D-serine were ~20 uM with post-injection values rising into the 12 mM range. This concentration is more than sufficient to achieve meaningful biological action as demonstrated in the studies described in this application. Ethanol alone does not alter D-serine concentration, suggesting that the increase in plasma level is attributable to the pre-injection of D-serine and minimally modulated by the injection of the ethanol.

Chronic, Sustained Administration.

Figure 4:
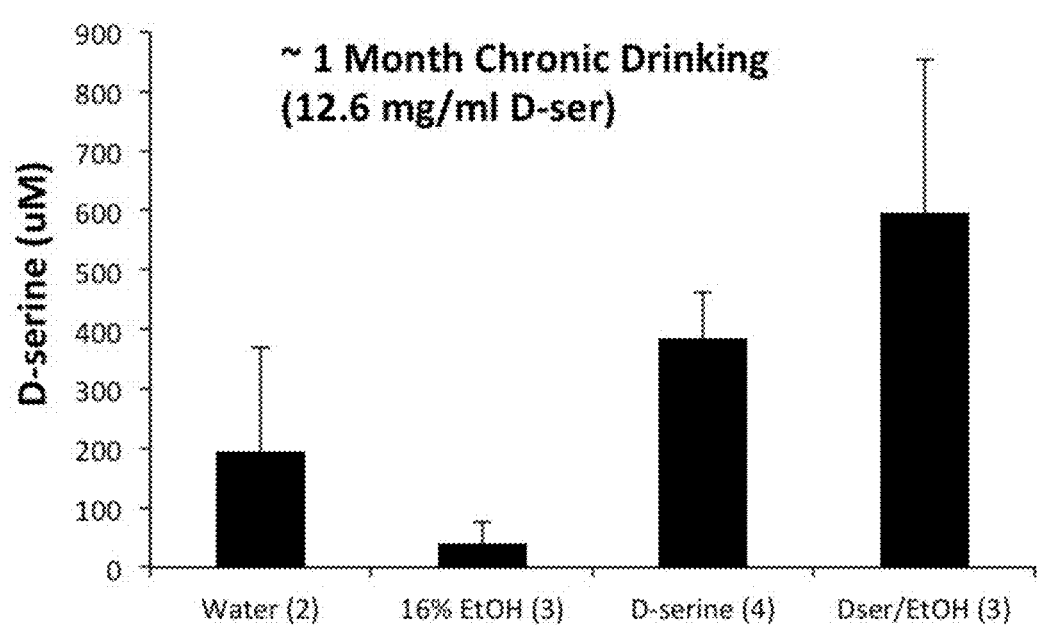
FIG. 4 demonstrates the blood plasma level of D-serine during chronic, sustained administration.
Figure 14:
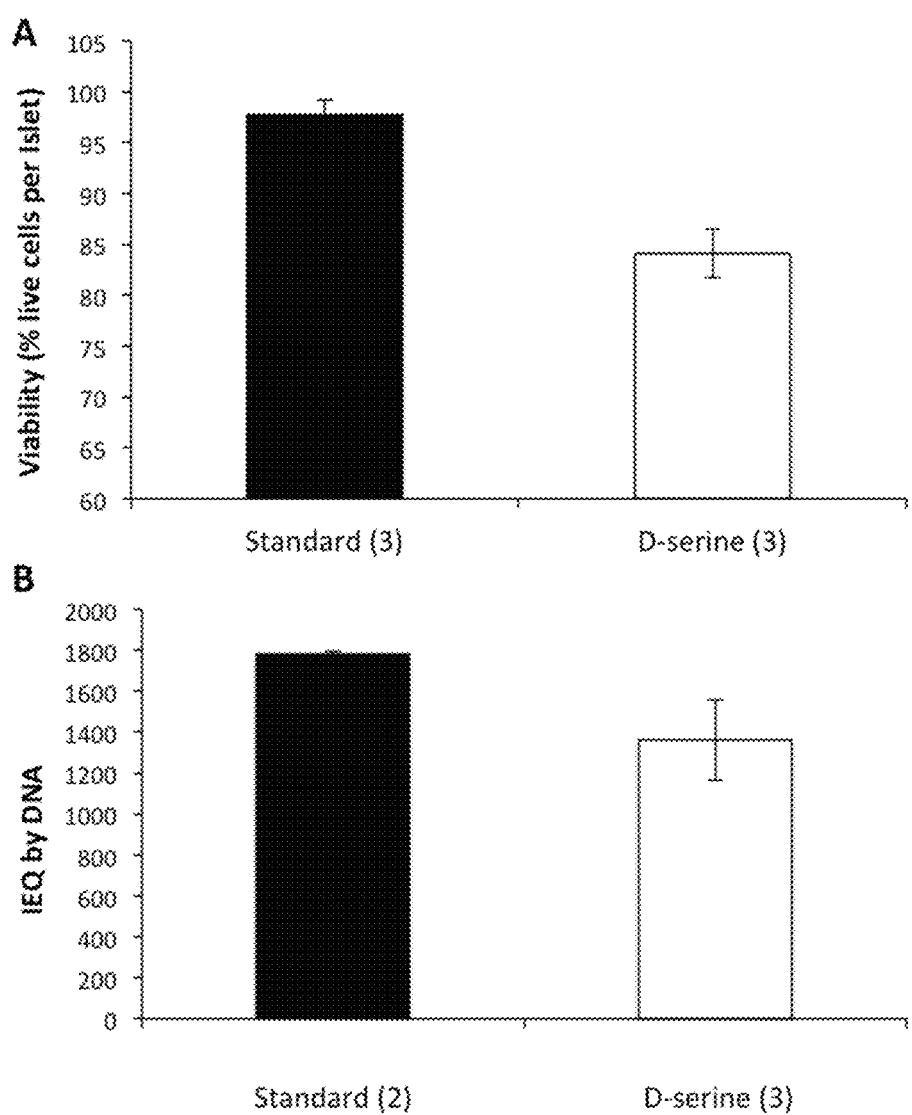
FIG. 14 illustrates the viability and survival rate of human islets cultured in a chronic, sustained high-concentration of D-serine for 1 week

The data from FIG. 4 were generated from an unpublished study of the impacts of D-serine on ethanol drinking. These data provide a presumable range of plasma D-serine levels achieved after a similar timeframe and method of D-serine administration to that used in the hyperglycemia experiments described in FIG. 2. Blood was collected from the facial vein and assayed via capillary electrophoresis as described above after mice (n=2-4 per condition as shown in the x-axis) had been presented with a choice of water vs. D-serine (or ethanol) drinking solution for 2 weeks and then 2 weeks of exclusively drinking treated solution according to their indicated treatment category. Mice that consumed D-serine containing solution (12.6 mg/mL) demonstrated an increased basal D-serine plasma level of 400-600 uM. This level is 2-3 times higher than that demonstrated by human patients undergoing D-serine oral therapy for metabolically-unrelated conditions in recent clinical trials (Emilov, M., et al. (2013), Schizophr Res 150: 604-5). It is also in the concentration range that resulted in cytotoxic islet cell damage subsequent to prolonged/tonic exposure in the experiments described in FIG. 14.

Figure 5:
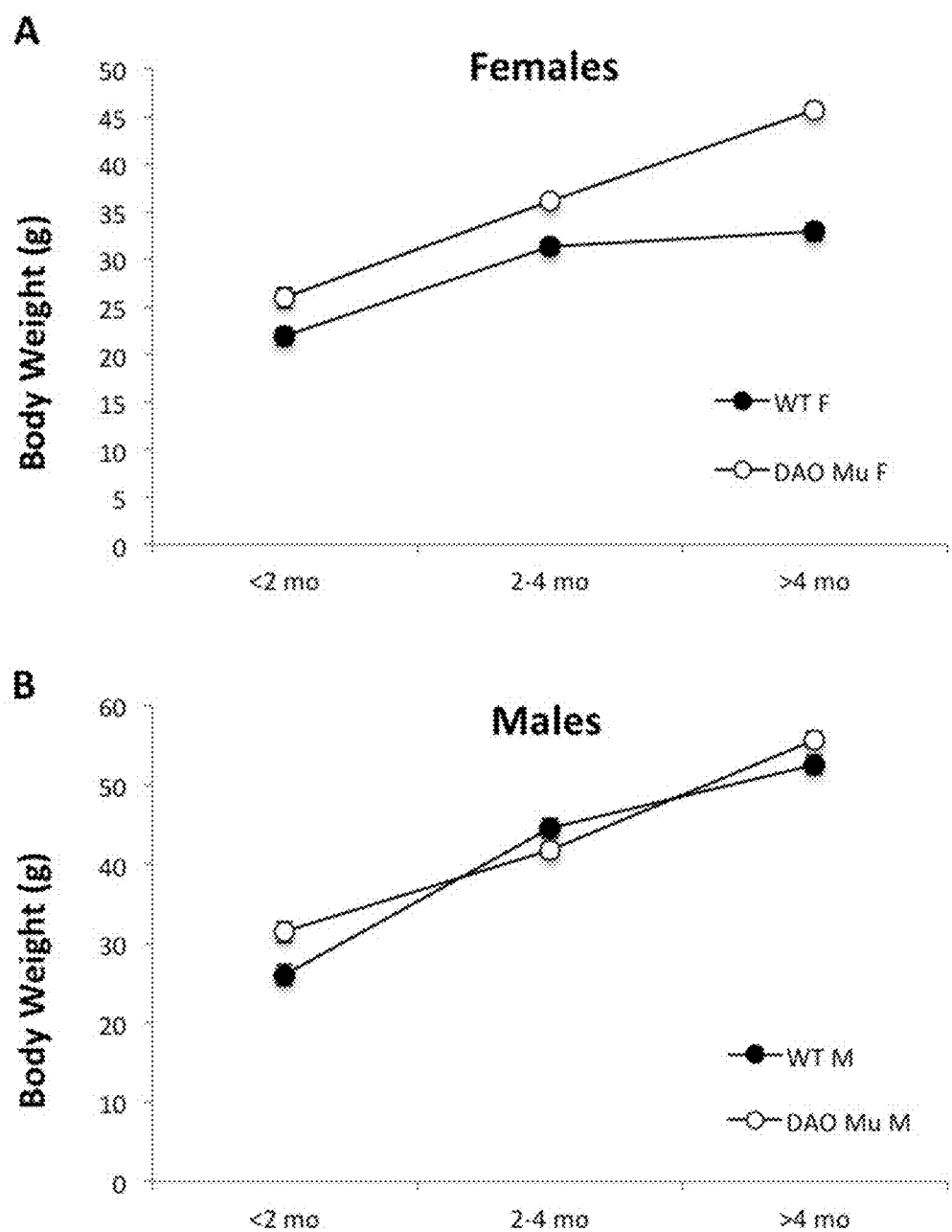
FIG. 5 shows the body weight of DAO mutant mice over age.

D. Study of the DAO Mutant Mouse Model of Elevated Endogenous D-Serine and Target Activity A colony of mice in which a deletion of the gene that produces D-amino acid oxidase (DAO), the catabolic enzyme that breaks down D-serine, was studied along with their wild-type controls. These mice have a slightly elevated systemic concentration of endogenous D-serine (from 2 to 10 uM in plasma (Hashimoto, A., (1993), Nsci Letters 152, 33-36)). The rat-based DAO mutant model shows a 10× increase in pancreatic D-serine content specifically (Miyoshi Y., et al., (2011), J Chromatography B, 879: 3184-3189). Additional evidence suggests that NMDA receptor activity is increased in these mice in a variety of tissues (e.g. retina (Gustafson, E., et al., (2013), J Neurophysiol 110, 2718-26), spinal cord (Wake, K., et al., (2005), Nsci Letters 297, 25-28)). The mice in this colony were weighed periodically over the course of 1.5 years. While all mice gained weight with development, as expected, mutant females gained more weight than their wild-type counterparts, developing a significant obese phenotype beyond 4 months of age (33±0.9 WT vs. 46±0.6 Mu in g body weight) (FIG. 5A). Body weights for mutant and wildtype male mice were similar at all ages. (FIG. 5B).

Figure 6:
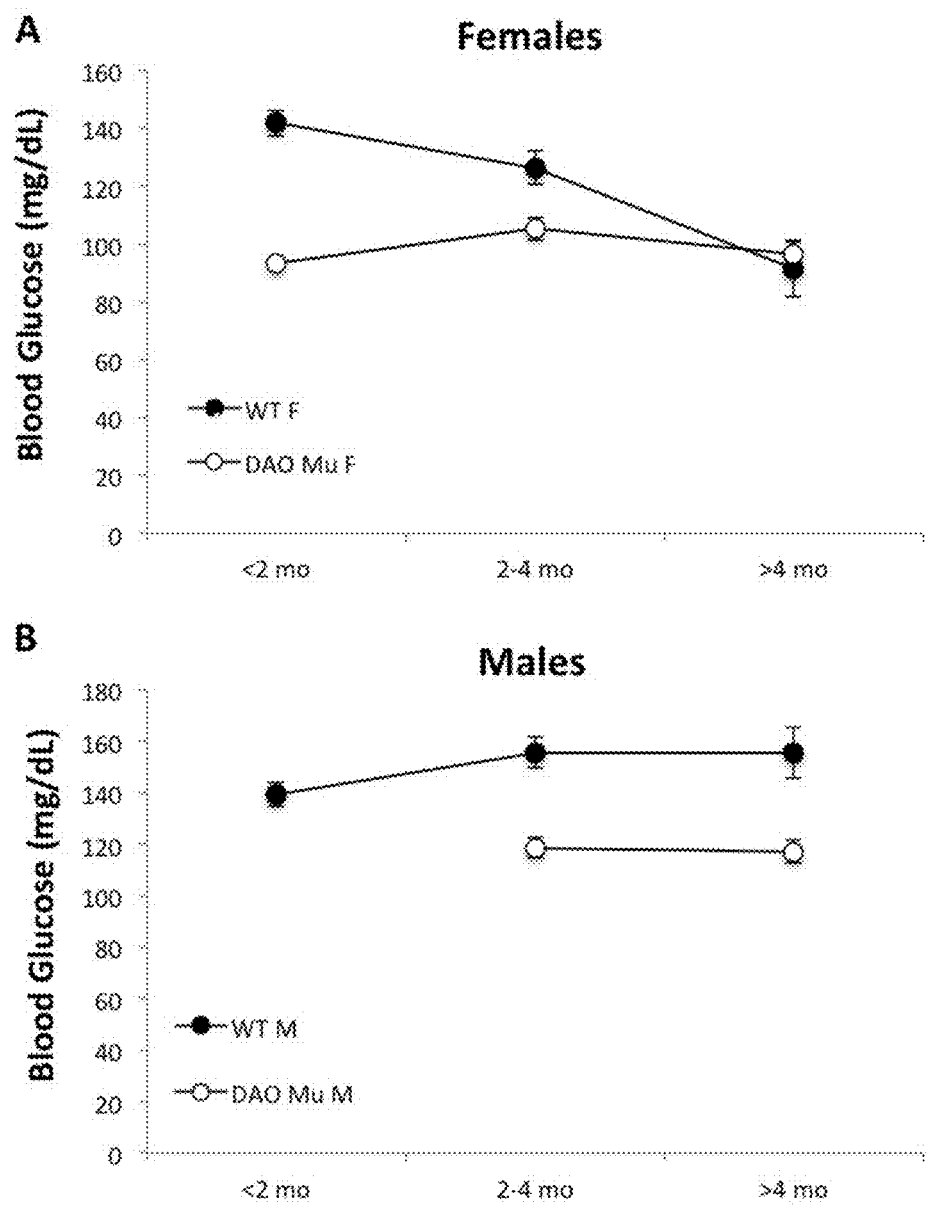
FIG. 6 shows the fasting blood glucose in DAO mutant mice over age.

Blood glucose levels of the mouse colonies were assessed on 5 separate occasions over the same time period, following a 4-6 hour fast. In this case, both DAO mutant males and females demonstrated basal level hypoglycemia at ages under 4 months compared to wildtype controls (For 2-4 months: 156±6 WT vs. 119±3.9 Mu male; 126±6.7 WT vs. 105±1.7 Mu female in mg/dL blood glucose) (FIG. 6A, B). But while hypoglycemia persisted for mutant males over 4 months old, mutant females demonstrated blood glucose levels similar to their wildtype counterparts in this older age range.

Figure 7A:
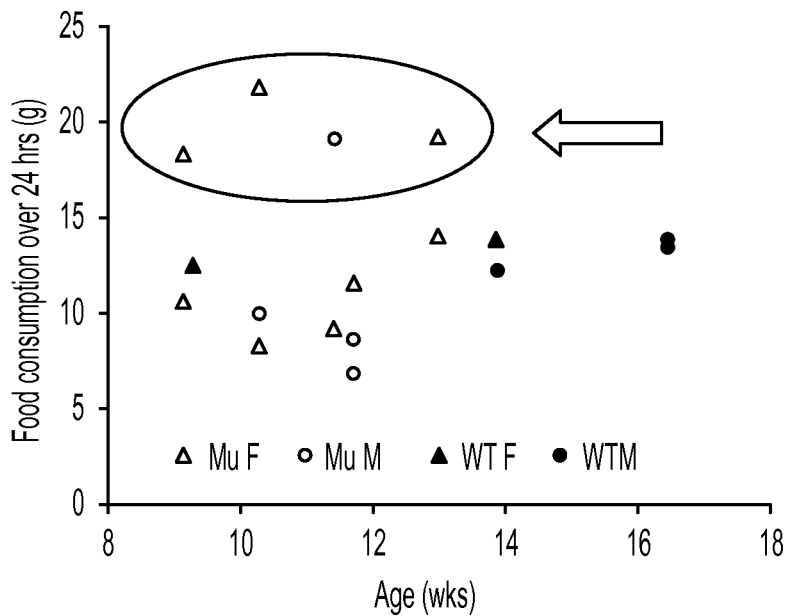
FIGS. 7A and 7B show the daily food and water consumption of some DAO Mu and WT mouse cages.
Figure 7B:
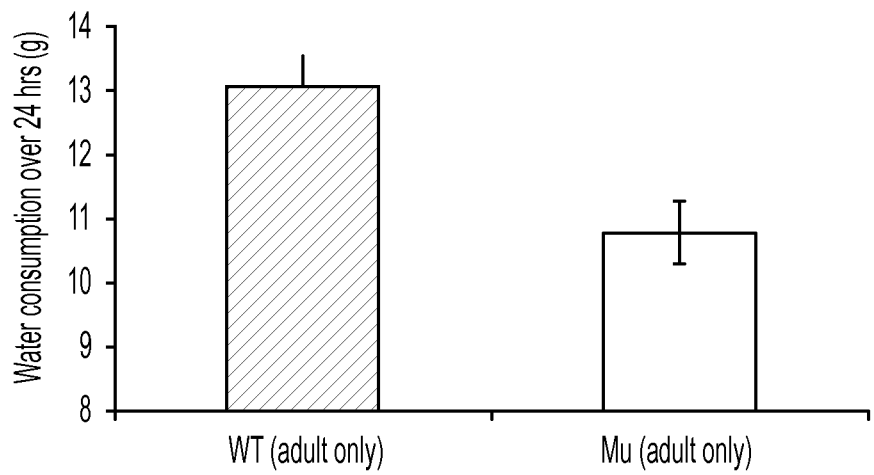

Certain mice in the DAO mutant colony described above showed a large increase in food consumption (hyperphagia) (FIG. 7A) and a decrease in average water drinking (7B). Changes in eating and drinking habits can be indicative of shifts in metabolic state. Excessive water drinking (polydipsia) is a common symptom of diabetes. Lower basal blood sugar and diminished water consumption in this DAO mutant mouse model of increased endogenous D-serine and NMDA receptor activity points towards an antidiabetic status.

E. Study of Hypothalamic Influence

Figure 8A:
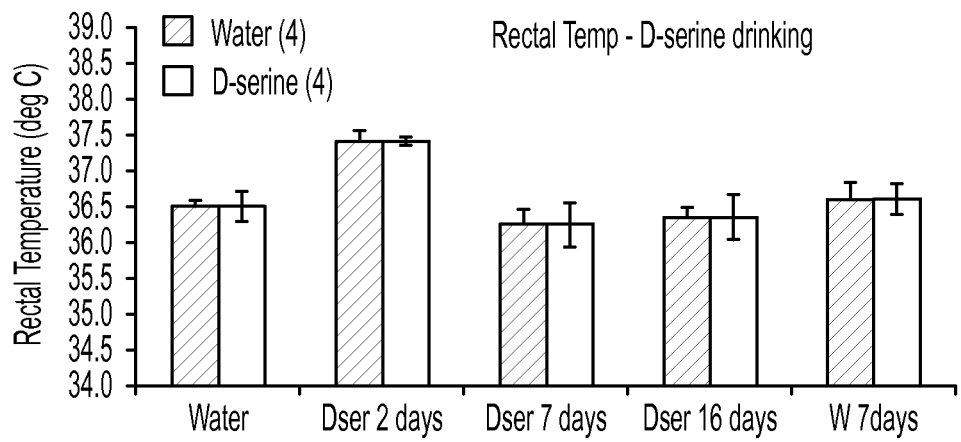
FIGS. 8A and 8B illustrate the effect of D-serine administration on core body temperature in wildtype and mutant DAO mice.
Figure 8B:
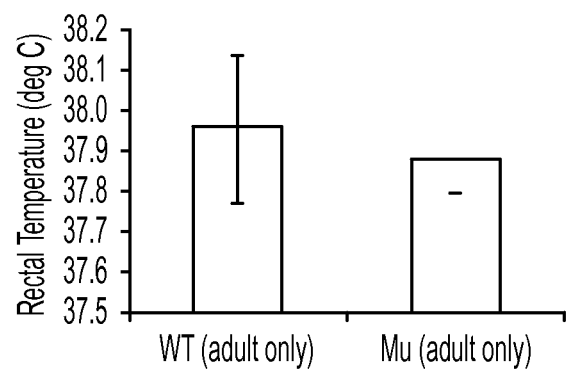
Figure 9:
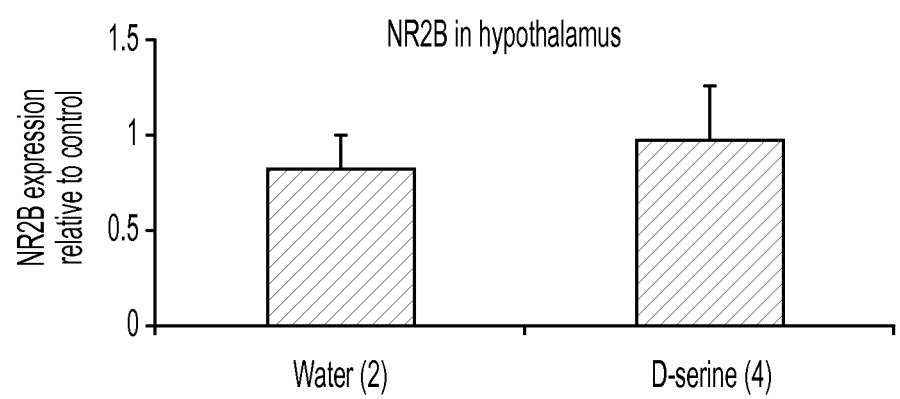
FIG. 9 shows a western blot analysis of mouse hypothalamus tissue after chronic, sustained, administration of D-serine.
Figure 10A:
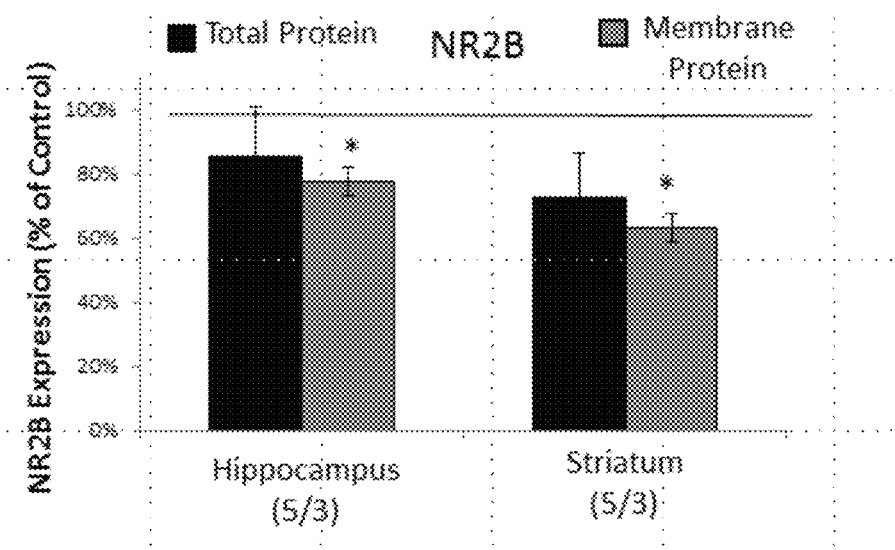
FIGS. 10A and 10B show western blots of hippocampal and striatal tissue of D-serine administered mice.
Figure 10B:
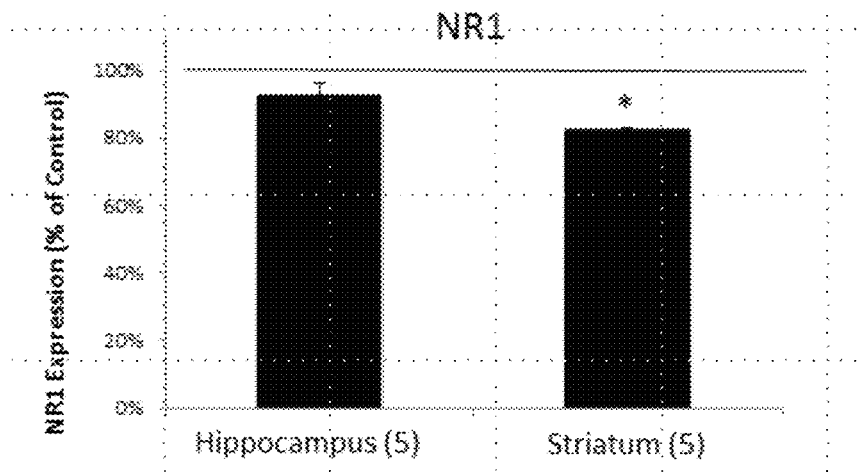

The hypothalamus is known to regulate metabolism through its influence on circadian rhythm, hunger, thirst, body temperature and glucose utilization among others. This study examined core body temperature and NMDA receptor protein expression to evaluate the potential influence of hypothalamic changes on the observed phenotypes. Core body temperature, determined by rectal thermometer, was stable throughout the chronic D-serine drinking experiment (FIG. 8A) and between wildtype and DAO mutant mice (FIG. 8B). A western blot analysis was run on some hypothalamic tissue from mice treated for 2.5 month of chronic D-serine drinking or water and no difference in the NMDA receptor subunit NR2B was observed (FIG. 9) despite significant expression changes observed in other brain areas, the hippocampus and striatum, from the same mice (FIG. 10). These data suggest that the hypothalamus may only play a limited role in the observed changes in murine blood sugar, body weight and eating/drinking habits.

Example 2

A. Human Islet Isolation and Culture

Living islets were isolated from the pancreas of a consenting organ donor via enzymatic digestion and isopycnic density gradient purification as previously described (Balamurugan, A N., et al., (2014) The Islets of Langerhans, $2^{nd}$ Edition, 1-25). This isolation was performed as a standard procedure by an experienced team at the Schulze Diabetes Institute of the University of Minnesota under GMP conditions. A portion of the total number of isolated islets were granted for these experiments after quality control testing and quantification. Islets were maintained in culture in supplemented Prodo media with a 5.5 mM glucose concentration in a T-flask at 37° C., 5% CO2. Half-volume media changes were performed every $3^{rd}$ day.

B. Study of Glucose Stimulated Insulin Release (GSIR)

After washing to remove culture media, approximate aliquots of 30 islet equivalents (IEQ, islet numbers normalized to an average size of 150 microns) were added to cell strainers immersed in 1.0 mL of 0-glucose solution. These were incubated at 37° C. for a 30 minute equilibration period. Strainers were then raised, drained and blotted before being transferred into a well containing 1.3 mL of low glucose (2.8 mM) solution. Within 30 seconds, a 300 uL time 0 sample was recovered from the well and the islets replaced into the remaining 1 mL solution for a 60 minute incubation period at 37° C. This procedure was repeated for subsequent wells containing 16.7 mM and then 28 mM glucose solutions. All well contents, both time 0 and post-stimulation samples, were stored at −80° C. until they could be assessed for insulin content via sandwich ELISA from a standard commercial mouse insulin ELISA kit. Insulin content, post-stimulation concentration minus the time 0 concentration, was normalized to the actual IEQ of each well, which was determined by Pico-green DNA assessment (Papas, K. K., et al., (2007), Am J Transplant 7, 707-13) of cell strainer contents recovered at the end of the final incubation. For a single day's experiment, 3× aliquots of islets were incubated in either a standard glucose series, glucose+100 uM D-serine, glucose+100 uM NMDA, glucose+100 uM D-serine+100 uM NMDA. While the concentration of glucose varied, the concentration of supplement did not. This experiment was repeated for 3 consecutive days drawing from the contents of 3 separately cultured flasks for a total of n=9 aliquots per experimental condition. The addition of NMDA to D-serine was considered necessary because the NMDA receptor requires simultaneous binding of a primary agonist (L-glutamate endogenously, NMDA here) and a co-agonist (D-serine) in order to be activated whereas the standard GSIR solutions did not contain any compound that would otherwise serve as the primary receptor agonist. It is expected, however, that such a compound would already be present in the background of the in vivo environment to allow the effective action of a singularly administered co-agonist agent.

Figure 11:
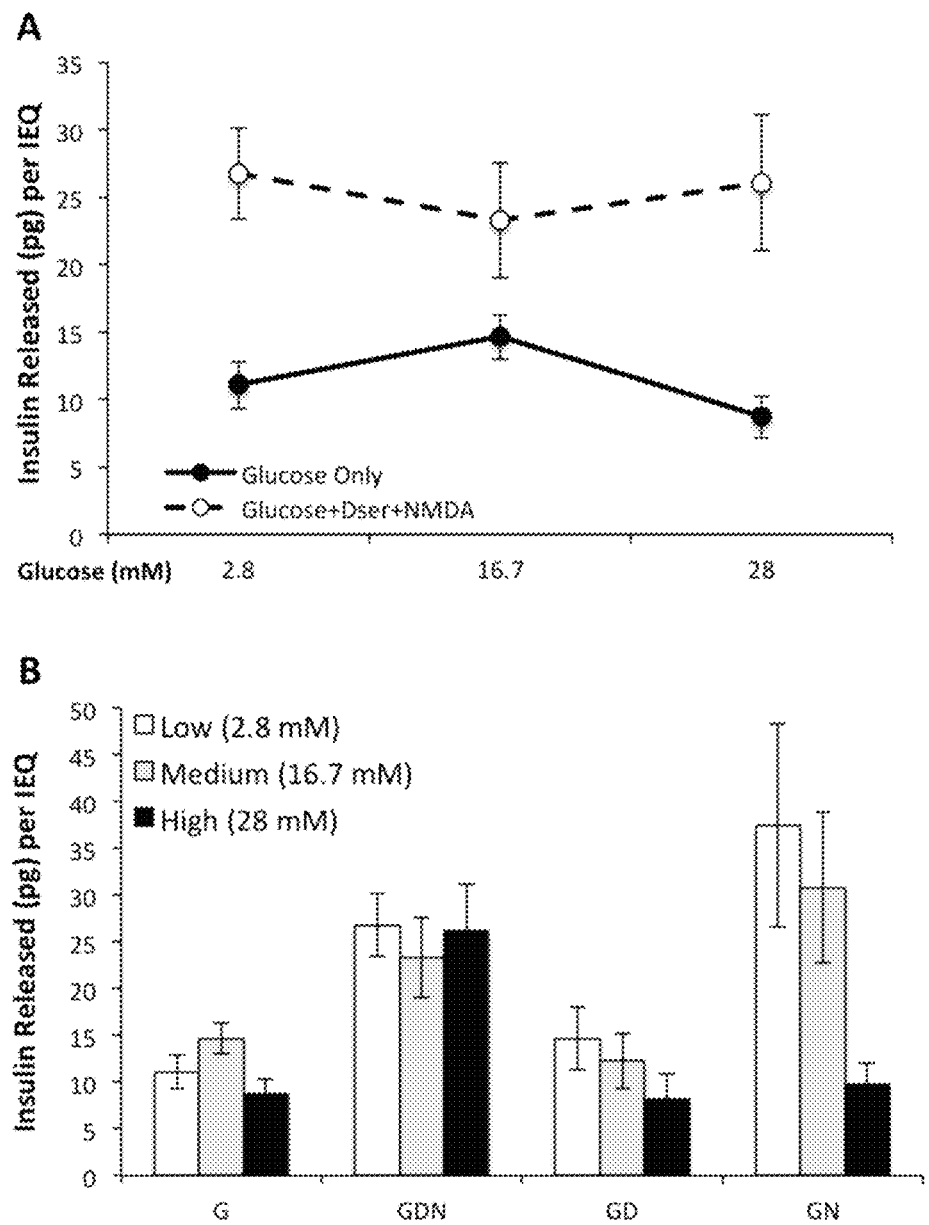
FIG. 11 shows the insulin secretion of human islets in response to glucose with or without D-serine and/or NMDA supplementation.

The data from this experiment show that the presence of NMDA receptor activating conditions (D-serine+NMDA) increased the magnitude of the stimulated insulin release at all glucose concentrations tested (total release 53±11.6 glucose only vs. 100±14.3 glucose+Dser+NMDA in pg of insulin per IEQ) (FIG. 11a). The magnitude of this effect was particularly intense at the low glucose concentration (11±1.8 glucose only vs. 27±3.4 glucose+Dser+NMDA), which represents basal systemic blood glucose levels, and in the $3^{rd}$ hour high glucose concentration condition (9±1.6 glucose only vs. 26±5.0 glucose+Dser+NMDA), during which control islets appeared to demonstrate glucose desensitization (Rustenbeck, I., (2002) Biochem Pharma 63, 1921-35) while Dser/NMDA exposed islets did not. It is also noteworthy that insulin levels for any given concentration were not much elevated above the level achieved by control islets stimulated at the 16.7 mM glucose concentration. As expected, D-serine alone had no effect on insulin secretion while NMDA alone had no effect on 2 out of 3 days tested (FIG. 11b). These data show that NMDA receptor activation through D-serine co-agonism increases insulin release from human islets at physiologically relevant glucose concentrations.

C. Study of Human Islet Viability

Figure 12:
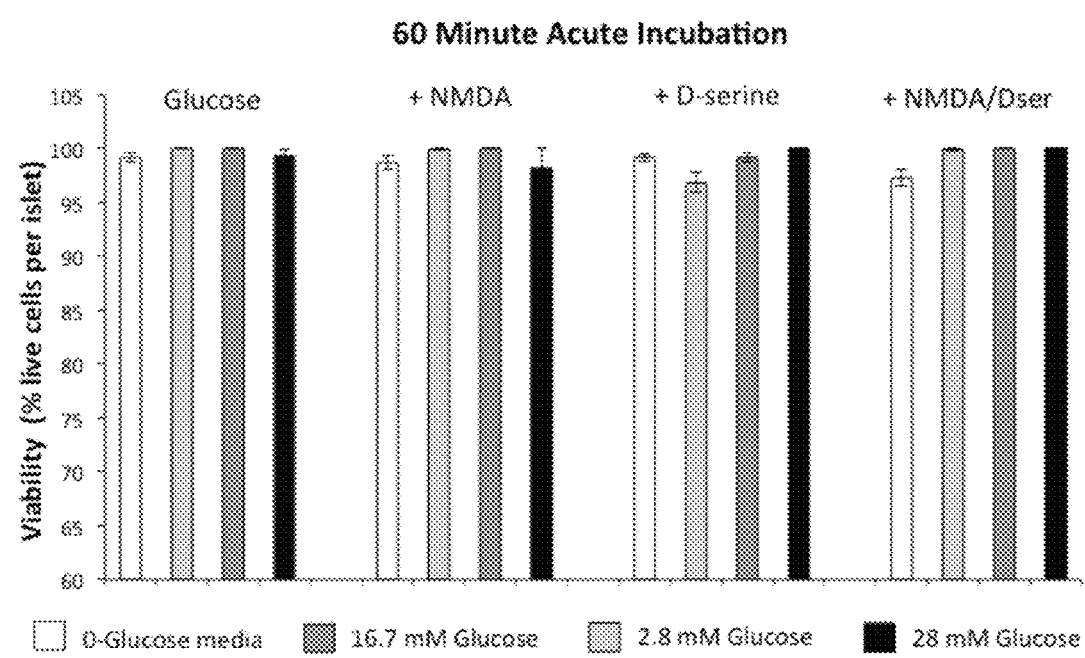
FIG. 12 demonstrates the viability of human islets exposed to glucose with or without D-serine and/or NMDA supplementation for 60 minutes.
Figure 13:
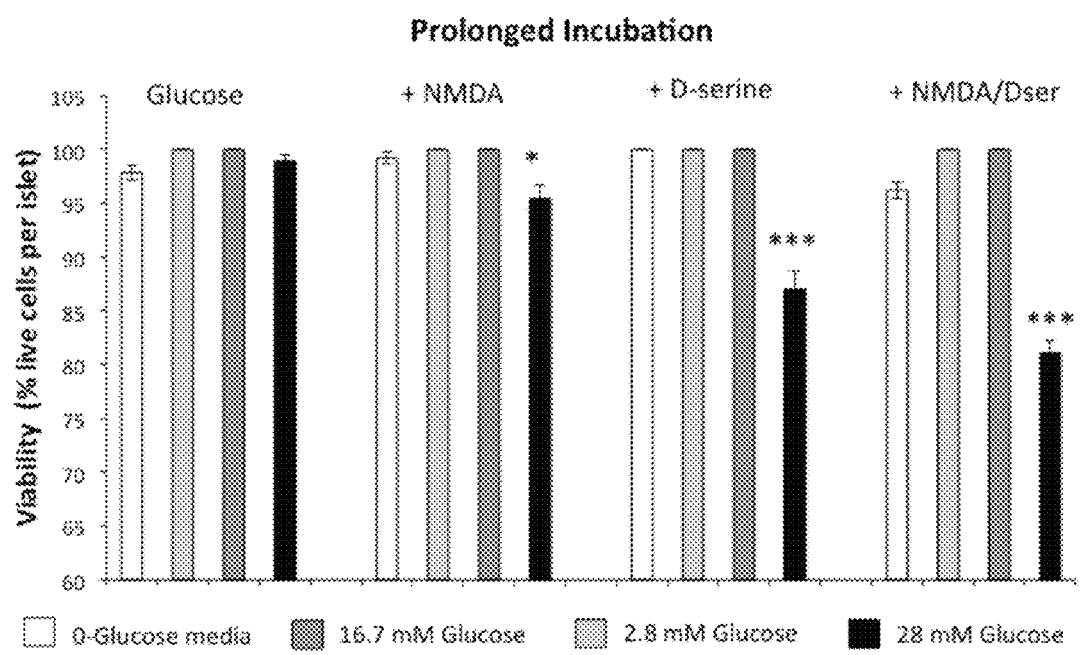
FIG. 13 demonstrates the viability of human islets exposed to glucose with or without D-serine and/or NMDA supplementation for a prolonged, multi-hour period.

After conditional incubations (described below), islets were placed in standard media for 2-8 hrs before viability assessment. The viability of islets was assessed by double staining an aliquot of ~25 islets with acridine orange (stains living cells) and propidium iodide (stains necrotic or apoptotic cells) (Bank, H. L., (1988) In Vitro Cell Dev Biol 24, 266-73). Each islet in the sample was evaluated under a fluorescent microscope and assigned a value for the % of live cells present and those numbers averaged for that sample. 3× samples per condition were assayed each day for 3 consecutive days and on one day in a follow-up experiment 1 week later. Prior to staining, aliquots were incubated for 60 minutes (FIG. 12, n=2 days) or 90 minutes (FIG. 13, n=2 days) in each solution type used in the GSIR incubations in addition to 100 uM concentrations of D-serine, NMDA or D-serine+NMDA alone (i.e. in 0 glucose). After 60 minutes of full concentration incubation, all islets showed near 100% viability (FIG. 12) indicating that none of the GSIR incubation conditions were damaging to the health of the islets. On the $3^{rd}$ day and in a subsequent follow-up experiment, islets were incubated for 90 minutes in the same solutions. In this case, viability was decreased only under those conditions with both the maximum glucose concentration (28 mM) and the addition of NMDA and/or D-serine with the most dramatic loss of viable islet cells (down to 81.1±1.1%) observed in the 28 mM glucose+100 uM NMDA+100 uM D-serine condition (FIG. 13). These data are consistent with the hypothesis that glucose and NMDA receptor activation work cooperatively on islet cells and that over-excitation of the beta cell may lead to excitotoxicity.

D. Study of Sustained High Concentration D-Serine on Human Islet Survival

Three flasks of isolated islets were cultured for 1 week in standard media or in media supplemented with 100 uM NMDA and 500 uM D-serine, representing a sustained exposure to high concentration D-serine, in the range observed in the plasma of mice that developed hyperglycemia after exclusively drinking D-serine for 1 week (FIG. 2). Fewer human islets were recovered from the flasks with persistent high D-serine (1527±147 standard vs. 1137±172 high D-serine in average pool IEQ) (FIG. 14B) as assessed by Pico-green DNA assay and those that were recovered displayed a lower average viability (98±1.4 standard vs. 84±2.4 high D-serine in % viable cells per islet) (FIG. 14A) than the contents of standard culture flasks. These data are consistent with the hypothesis that persistent high NMDA receptor stimulation, as opposed to acute transient activation, is damaging to islet survival and may be a contributing cause to the development of hyperglycemia in mice from FIG. 2. The proposed mechanism of action for this effect, cytotoxicity from sustained hyperexcitation of the β-cell, has also been a proposed mechanism of chronic hyperglycemia induced β-cell apoptosis (Tamovsky-Babeay, S., et al., (2014), Cell Metab 19: 109-21).

Example 3

The following illustrate representative pharmaceutical dosage forms, containing an NMDA receptor activator (e.g., D-serine) ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a dysregulated blood glucose disorder in a mammal in need thereof comprising administering an effective amount of an N-methyl-D-aspartate receptor activator or a pharmaceutically acceptable salt thereof to the mammal in need thereof.

2. The method of claim 1, wherein the N-methyl-D-aspartate receptor activator is a functional agonist at the glycine binding site on the N-methyl-D-aspartate receptor.

3. The method of claim 1, wherein the N-methyl-D-aspartate receptor activator binds to the glycine binding site on the N-methyl-D-aspartate receptor.

4. The method of claim 1, wherein the N-methyl-D-aspartate receptor activator is D-serine, D-cycloserine or glycine or a pharmaceutically acceptable salt thereof.

5. The method of claim 1, wherein the N-methyl-D-aspartate receptor activator is D-serine or a pharmaceutically acceptable salt thereof.

6. The method of claim 1, wherein the dysregulated blood glucose disorder is hyperglycemia.

7. The method of claim 6, wherein the hyperglycemia is caused by pancreatitis, pancreatic cancer, hyperthyroidism, Cushing's syndrome, glucagonoma, pheochromocytoma, stress episodes, medication side-effects or pregnancy or insulin resistance or insulin deficiency.

8. The method of claim 6, wherein the hyperglycemia is caused by insulin resistance.

9. The method of claim 1, wherein the dysregulated blood glucose disorder is diabetes.

10. The method of claim 1, further comprising administering insulin to the mammal.

11. The method of claim 10, wherein the N-methyl-D-aspartate receptor activator or the pharmaceutically acceptable salt thereof and the insulin are co-administered.

12. The method of claim 1, further comprising administering a D-amino acid oxidase inhibitor or a pharmaceutically acceptable salt thereof to the mammal.

13. The method of claim 1, further comprising administering a antidiabetic agent or a pharmaceutically acceptable salt thereof to the mammal.

14. A pharmaceutical composition comprising an N-methyl-D-aspartate receptor activator or a pharmaceutically acceptable salt-thereof, insulin and a pharmaceutically acceptable carrier.

15. The pharmaceutical composition of claim 14, wherein the N-methyl-D-aspartate receptor activator is D-serine, D-cycloserine or glycine or a pharmaceutically acceptable salt thereof.

16. The pharmaceutical composition of claim 14, wherein the N-methyl-D-aspartate receptor activator is D-serine or a pharmaceutically acceptable salt thereof.

17. The pharmaceutical composition of claim 14, further comprising a D-amino acid oxidase inhibitor or a pharmaceutically acceptable salt thereof.

\* \* \* \* \*